United States Patent [19]

Rustad

[11] Patent Number: 4,973,731
[45] Date of Patent: Nov. 27, 1990

[54] DI-T-BUTYLPHENYL ALKYL AND BENZYL ETHER NITRILES

[75] Inventor: Mark A. Rustad, Afton, Minn.

[73] Assignee: Riker Laboratories, Inc., St. Paul, Minn.

[21] Appl. No.: 41,703

[22] Filed: Apr. 23, 1987

[51] Int. Cl.$^5$ .......................................... C07C 121/16
[52] U.S. Cl. ................................. 558/389; 548/251; 548/253
[58] Field of Search ........................................ 558/389

[56] References Cited

U.S. PATENT DOCUMENTS

| | | | |
|---|---|---|---|
| 2,819,197 | 1/1958 | Santmeyer et al. | 558/389 |
| 2,974,160 | 1/1961 | Heininger | 558/389 |
| 3,674,836 | 7/1972 | Creger | 260/473 |
| 4,675,334 | 6/1987 | Steggles et al. | 514/381 |

FOREIGN PATENT DOCUMENTS

| | | |
|---|---|---|
| 25648 | 2/1967 | Australia . |
| 1272235 | 2/1969 | Fed. Rep. of Germany . |
| 853099 | 11/1960 | United Kingdom . |
| 2143817A | 2/1985 | United Kingdom . |

OTHER PUBLICATIONS

Chemical Abstracts, 1986, 106, 85170K.
G. G. Cross et al., Can. J. Chem., 62(12), 2803–12.

*Primary Examiner*—David B. Springer
*Attorney, Agent, or Firm*—Donald M. Sell; Walter N. Kirn; Robert W. Sprague

[57] ABSTRACT

Novel compounds which are di-t-butylphenyl alkyl or benzyl ethers which alkyl or benzyl group is substituted by an acidic group are useful an antiallergic agents. Synthetic intermediates for making such compounds are also disclosed.

1 Claim, No Drawings

DI-T-BUTYLPHENYL ALKYL AND BENZYL ETHER NITRILES

TECHNICAL FIELD

This invention relates to 3,5-di-t-butylphenyl alkyl or benzyl ethers which alkyl or benzyl group is substituted by an acidic group. The acidic group may be carboxyl, tetrazolyl or carboxamidotetrazolyl. This invention further relates to pharmaceutical compositions containing such compounds, pharmacological methods for using such compounds and synthetic intermediates for preparing such compounds.

BACKGROUND OF THE INVENTION

Some 3,5-di-t-butylphenyl alkyl ethers wherein the alkyl group contains a carboxyl substituent are known in the art.

Ger. Offen. DE No. 1925423 discloses 5-(3,5-di-butylphenoxy)-2,2-dimethylvaleric acid as being useful for lowering serum glycerides.

G. G. Cross et al., Can. J. Chem., 62(12), 2803–12, describes the nitration of 3,5-di-t-butylphenoxyacetic acid and alpha-(3,5-di-t-butylphenoxy) isobutyric acid to form nitrodienones and nitrodienes.

DETAILED DESCRIPTION OF THE INVENTION

The present invention relates to compounds of Formula I:

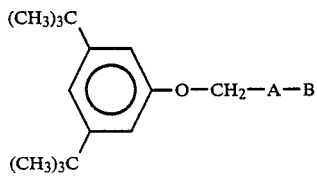

wherein
A is phenylene or an alkylene group containing two to about seven carbon atoms; and
B is carboxyl, tetrazolyl or carboxamidotetrazolyl;
and a derivative of a compound wherein B is carboxyl selected from the group consisting of lower alkyl esters, (lower)alkylamino(lower)alkyl esters, pharmaceutically acceptable (lower)alkylamino(-lower)alkyl ester acid-addition salts and pharmaceutically acceptable carboxylate salts;
and a derivative of a compound wherein B is tetrazolyl or carboxamidotetrazolyl selected from pharmaceutically acceptable alkali metal and alkaline earth salts of the tetrazolyl moiety.

Compounds of Formula I are useful to inhibit bronchoconstriction due to allergic response.

The present invention also provides novel compounds of Formula II

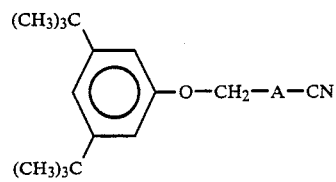

wherein A is as defined previously.

Compounds of Formula II are useful synthetic intermediates for preparing the compounds of Formula I.

By "lower" as used in connection with "alkyl" is meant that such groups contain one to about four carbon atoms.

In the compounds of Formula I wherein B is tetrazolyl or carboxamidotetrazolyl, two tautomeric forms of tetrazolyl exist as is known to those skilled in the art.

It is well known to the art that pharmaceutically acceptable salts such as alkali metal, alkaline earth, aluminum and other metal and amine salts of pharmaceutically active acids are the equivalents of the acids in terms of activity, and in some cases may even offer advantages in absorption, formulation and the like. Pharmaceutically acceptable carboxylate salts of the compounds of the invention which contain carboxyl as B are prepared by reaction of the acid with a base and subsequent evaporation to dryness, preferably under mild conditions. The base may be organic, for example, sodium methoxide or an amine, or inorganic, for example, sodium hydroxide. Alternatively, the cation of a carboxylate salt, for example, sodium may be displaced by a second cation such as calcium or magnesium when the salt of the second cation is more insoluble in a selected solvent.

Other useful derivatives of the compounds of the invention which contain carboxyl as B include alkyl esters, alkylaminoalkyl esters, and salts of the latter. In the ester derivatives, the hydrogen portion of the carboxylic acid group is replaced with an alkyl or substituted alkyl.

Ester derivatives may be obtained by alkylation of an alkali metal salt of the compound in dimethylformamide with an alkyl iodide or dialkylaminoalkylchloride or by the use of other standard synthetic methods.

Pharmaceutically acceptable alkali metal and alkaline earth salts may also be prepared of compounds of Formula I wherein B is tetrazolyl or carboxamidotetrazolyl by methods known to those skilled in the art.

The compounds of Formula I may be prepared in accordance with the procedures of the Reaction Scheme shown below wherein A is as defined above.

REACTION SCHEME

REACTION SCHEME

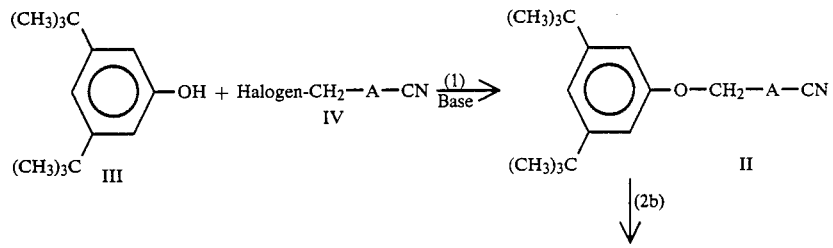

REACTION SCHEME -continued

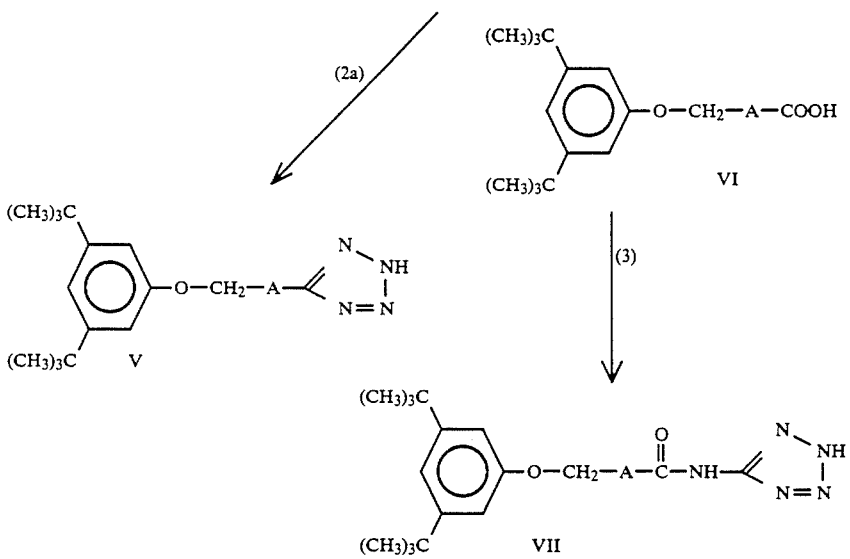

In step (1), the known compound 3,5-di-t-butylphenol (III) is reacted with a halonitrile of Formula IV to provide a nitrile of Formula II. One equivalent of 3,5-di-t-butylphenol (III) is combined with one equivalent of a halonitrile of Formula IV and with one equivalent of a base, such as sodium hydroxide, in the presence of a polar solvent such as dimethylformamide. The reaction is heated at about 120° C. for about sixteen to about forty hours. Halonitriles of Formula IV are known compounds or may be prepared using known methods. Examples of halonitriles of Formula IV are alpha-bromo-o-tolunitrile, alpha-bromo-m-tolunitrile, 5-chlorovaleronitrile, 7-bromoheptanenitrile and the like. The compounds of Formula II may be readily isolated and purified, for example, by recrystallization.

In step (2a), one equivalent of the intermediate of Formula II is combined with 3.0 to 6.0 equivalents of sodium azide, 3.0 to 6.0 equivalents of ammonium chloride and 1.0 equivalent of lithium chloride in the presence of a polar solvent such as dimethylformamide. The reaction mixture is heated in a stoppered flask at about 120° C. for sixteen to sixty-four hours. The products of Formula V, which is a subgenus of Formula I, may be readily isolated and purified using conventional techniques, for example, chromatography or recrystallization.

In step (2b) the nitrile of Formula II is hydrolyzed to the acid of Formula VI. In an inert atmosphere, one equivalent of the nitrile is combined with two to ten equivalents of a base, such as potassium hydroxide, in the presence of a polar solvent such as 2-methoxyethanol. The reaction is heated at a temperature of 125° to 145° C. for about sixteen to ninety hours until hydrolysis is complete. The products of Formula VI, which is a subgenus of Formula I, may be readily isolated and purified using standard techniques.

In step (3), the acids of Formula VI are converted to the carboxamidotetrazoles of Formula VII. One equivalent of an acid of Formula VI is combined with one equivalent of 5-aminotetrazole and two equivalents of thionyl chloride in pyridine. The reaction mixture is allowed to stir at room temperature for about thirty to ninety minutes. Alternatively, the acid and the aminotetrazole may be combined with phosphorous trichloride in toluene. The products of Formula VII, which is a subgenus of Formula I, may be readily isolated and purified using conventional techniques.

The activity of compounds of Formula I may be demonstrated readily by in vivo testing. The in vivo test used may be any of those known to those skilled in the art. Preferably, bronchoconstriction in sensitized guinea pigs is measured upon antigen challenge. Active compounds are those which demonstrate an intraperitoneal $ED_{40}$ of 100 mg per kg or less. Most preferred compounds are active at 25 mg per kg. This test is described in broad terms by Piechuta, et al., Immunology, 38, 385 (1979), and more specifically by Hammerbeck and Swingle, Int. Archs. Allergy Appl. Immun. 74, 84–90 (1984), both publications being incorporated herein by reference. It was used in a modified form as follows: Male Hartley guinea pigs (250–600 g) were pretreated with an antihistamine, e.g., chlorpheniramine, then dosed intraperitoneally with a compound of the invention at a level of about 1 to 40 mg/kg 15 minutes prior to challenge. The animals were placed under an inverted dessicator jar (18 × 14 cm) with a constant flow of air coming into the chamber from a compressed-air source to prevent hypoxia and were aerosol challenged with either water or ovalbumin at a concentration of 10 mg per ml. Air flow leaving the chamber and fluctuations due to respiration were monitored through a separate outlet with a Fleisch No. 0000 pneumotachograph (available from Beckman Instruments, Inc., Schiller Park, Ill.) coupled to a Beckman Type R dynograph (available from Beckman Instruments, Inc.). Aerosolization through a third outlet was made via a No. 4 DeVilbiss nebulizer (available from The DeVilbiss Company, Somerset, Pa.) for 90 seconds at 150 mm Hg. The characteristic respiratory patterns observed were summations of two air exchange processes occurring simultaneously in the chamber. One exchange process was due to inspiration and expiration of air into and out of the animal, while the other exchange was due to the air into and out of the chamber due to respiratory movements. The tracing obtained was the mechanical representation of the summation of those flows. Superimposed on the tracings was a characteristic spiking ('notching'), which appears to be an exaggerated expiratory movement, the frequency of which correlates with the severity of the bronchoconstrictive reaction. The frequency of notching for 15-minute periods beginning 4 minutes after the beginning of the aerosol challenge was used for comparing various treatments. Effects were considered significant if the t value achieved $p<0.05$.

The oral activity of compounds of Examples 7 and 14 was demonstrated using the Konzett-Rossler in vivo test method. The activity was determined according to the procedure which follows. The Konzett-Rossler technique (H. Konzett and R. Rossler, Naunyn-Schmiedbergs Arch. Pharmakol., 195, 71–74 (1940), incorporated herein by reference, was used to assess the effect of compounds on antigen challenge of male Hartley strain guinea pigs (350–500 g). Fourteen days after sensitization with ovalbumin (50 mg/kg intraperitoneally) guinea pigs were anesthetized with pentobarbital (70 mg/kg intraperitoneally) and spontaneous respiration was eliminated with succinylcholine (2 mg/kg intraperitoneally). The trachea was cannulated and respiration was maintained under positive pressure with a miniature ventilator (5 ml/breath, 87 breaths/minute, 10 cm water). Bronchoconstrictor responses were represented as increased excursions of the tracing on a physiological recorder of air overflow to the lungs measured by a pneumotachograph in series with a differential pressure transducer. The guinea pigs were pretreated with an antihistamine, for example, chlorpheniramine, and then dosed orally at a level of about 5 to 40 mg/kg with a suspension of a compound in 4% aqueous acacia. The animals were challenged with ovalbumin (300 micro-g/kg intravenously) thirty minutes later.

The compounds of the invention were also tested for their ability to inhibit leukotriene biosynthesis. Active compounds are those which exhibit an $IC_{50}$ of 100 micromolar or less, and preferably less than 25 micromolar. Most preferred compounds exhibit an $IC_{50}$ of 10 micromolar or less. The compounds were tested in either intact cells or in cell sonicate. The intact cell assay is similar to that described by Verhagen et al., FEBS Letter 168, 23–28 (1984), incorporated herein by reference. Human leukocytes were prepared using standard procedures. The cells were incubated in pH 7.4 Tris buffer containing 5 millimolar calcium chloride and 5 millimolar glutathione. After vehicle or drug incubation, the cells were activated with the calcium ionophore A 23187 (4 micrograms per ml). After 15 minutes at room temperature, the cells were centrifuged and the supernatants were stored for assay of $LTC_4$ content by radioimmunoassay. The cell sonicate assay utilizes the cell free leukotriene biosynthesis system of M. Steinhoff et al., Biochim. Biophy. Acta. 68, 28 (1980), incorporated herein by reference, which consists of homogenized rat basophil leukemia cells. Leukotriene synthesis was initiated by the addition of arachidonate. Solutions were centrifuged and supernatants assayed using a radioimmunoassay developed as described by Aeringhaus et al., FEBS Letters 146, 111–114, incorporated herein by reference. Drugs were dissolved in ethanol or dimethyl sulfoxide and preincubated for five minutes. Phenidone was used as a positive control.

The compounds of Examples 2, 8, 11, 13, 14, 16 and 17 were found to be inhibitors of leukotriene biosynthesis using the in vitro test method described above.

Thus, compounds of Formula 1 are antiallergic agents exhibiting in vivo activity in mammals. The pharmaceutical compositions of the present invention will contain sufficient compound of Formula I in a dosage form suitable for inhibiting bronchoconstriction due to an allergic response. The effective concentration of the Formula I compound in the composition will vary as required by the mode of administration, dosage form and level desired.

For treating pulmonary conditions such as asthma, the mode of administration may be oral, parenteral, by inhalation, by suppository and the like. Suitable oral dosage forms are tablets, elixirs, emulsions, solutions, capsules, including delayed or sustained release dosage forms. Dosage forms for administration by inhalation include aerosols and sprays and may be administered in metered doses.

For treating allergies or allergic reactions, the compound of Formula I may be administered by any conventional mode, for example, orally, parenterally, topically, subcutaneously, by inhalation and the like. The oral and parenteral dosage forms are as described for pulmonary treatment. The topical application dosage forms include ointments, sprays, controlled release patches, powders, solutions and the like.

In preparing suitable dosage forms, conventional compounding procedures and ingredients, for example, diluents, carriers, etc. may be used. Examples of suitable solid carriers are lactose, terra alba, sucrose, talc, gelatin, agar, pectin, acacia, magnesium stearate, stearic acid and the like. Examples of suitable liquid carriers are syrup, peanut oil, olive oil, water, a polyethylene glycol such as "PEG 400" (available from Union Carbide) and the like. Similarly, the carrier or diluent can include any time delay material well known to the art, such as glyceryl monostearate or glyceryl distearate, these being useful alone or, for example, in combination with wax.

The following examples are provided to illustrate the invention, but are not intended to be limiting thereof.

EXAMPLE 1

Preparation of 4-(3,5-Di-t-butylphenoxymethyl)-1-benzenecarbonitrile

A mixture of 5.1 g (25 mmole) of 3,5-di-t-butylphenol, 4.2 g (25 mmole) of alpha-bromo-p-tolunitrile, 1.0 g (25 mmole) sodium hydroxide and 75 ml of dimethylformamide was heated at 120° C. for about sixteen hours. The mixture was poured into 700 ml of water to give an oil which rapidly solidified. The solid was collected, rinsed with water, and recrystallized once from ethanol and twice from hexane to give 1.0 g of white crystalline 4-(3,5-di-t-butylphenoxymethyl)-1-benzenecarbonitrile, m.p. 118°–121° C. Analysis: Calculated for $C_{22}H_{27}NO$: %C, 82.2; %H, 8.5; %N, 4.4; Found: %C, 82.7; %H, 8.6; %N, 4.1.

EXAMPLE 2

Preparation of 5-{4-[(3,5-Di-t-butylphenoxy)methyl]phenyl}tetrazole

A mixture of 3.21 g (0.01 mole) of 4-(3,5-di-t-butylphenoxymethyl)-1-benzenecarbonitrile, 1.95 g (0.03 mole) of sodium azide, 1.60 g (0.03 mole) of ammonium chloride, 0.42 g (0.01 mole) of lithium chloride and 25 ml of dimethylformamide was heated at 120° C. in a stoppered flask for about sixty-four hours. The mixture was poured into 500 ml of water. The resulting precipitate was collected, rinsed with water and recrystallized from ethanol to give 2.7 g of white crystalline 5-{4-[(3,5-di-t-butylphenoxy)methyl]phenyl}tetrazole, m.p. 253°–255° C. Analysis: Calculated for: $C_{22}H_{28}N_4O$: %C, 72.5; %H, 7.7; %N, 15.4; Found: %C, 72.5; %H, 7.9; %N, 15.0.

EXAMPLE 3

Preparation of 4-(3,5-Di-t-butylphenoxymethyl)benzoic Acid

A mixture of 3.21g (0.01 mole) of 4-(3,5-di-t-butylphenoxymethyl)-1-benzenecarbonitrile, 6.23 g (0.1 mole) of potassium hydroxide (90%) in 5 ml of water, and 30 ml of 2-methoxyethanol was heated at reflux under a nitrogen atmosphere for about sixteen hours. The mixture was allowed to cool to room temperature before being poured into cold 5% hydrochloric acid. The resulting precipitate was collected, rinsed with water, air dried and recrystallized from ethanol to give 2.6 g of cream colored crystalline 4-(3,5-di-t-butylphenoxymethyl)benzoic acid, m.p. 212°–215° C. Analysis: Calculated for $C_{22}H_{28}O_3$: %C, 77.6; %H, 8.3; Found: %C, 77.6; %H, 8.5.

EXAMPLE 4

Preparation of 4-(3,5-Di-t-butylphenoxymethyl)-N(tetrazol-5-yl)benzamide

A solution of 2.00 g (5.9 mmole) of 4-(3,5-di-t-butylphenoxymethyl)benzoic acid and 0.61 g (5.9 mmole) of 5-aminotetrazole in 20 ml of pyridine was treated with a dropwise addition of 1.40 g (11.8 mmole) of thionyl chloride. The solution was stirred for one and a half hours before being poured into 150 ml of water. The resulting precipitate was collected, rinsed with water, air dried and recrystallized from aqueous dimethylformamide to give 1.4 g of white solid 4-(3,5-di-t-butylphenoxymethyl)-N-(tetrazol-5-yl)benzamide, m.p. >290° C. Analysis: Calculated for: $C_{23}H_{29}N_5O_2$; %C, 67.6; %H, 7.1; %N, 17.2; Found: %C, 67.8; %H, 7.3; %N, 17.6.

EXAMPLE 5

Preparation of 2-(3,5-di-t-butylphenoxymethyl)-1-benzenecarbonitrile

Using the method of Example 1, 20.6 g (0.10 mole) of alpha-bromo-o-tolunitrile was reacted with 3,5-di-t-butylphenol to give 9.9 g of white crystalline 2-(3,5-di-t-butylphenoxymethyl)-1-benzenecarbonitrile.

EXAMPLE 6

Preparation of 5-{2-[(3,5-Di-t-butylphenoxy)methyl]phenyl]-phenyl} tetrazole

A mixture of 3.21 g (0.01 mole) of 2-(3,5-di-t-butylphenoxymethyl)-1-benzenecarbonitrile, 1.95 g (0.03 mole) of sodium azide, 1.60 g (0.03 mole) of ammonium chloride, 0.42 g (0.01 mole) of lithium chloride and 25 ml of dimethylformamide was heated at 120° C. in a stoppered flask for about sixteen hours. The reaction mixture was poured into 200 ml of water and then extracted with 150 ml of chloroform. The chloroform extract was dried with magnesium sulfate and then evaporated to give an oil. The oil was rapidly chromatographed on 50 g of silica gel using 98:2:0.25 chloroform:methanol:acetic acid as the eluant. The fractions containing product were combined and evaporated to give a yellow oil which was recrystallized from a mixture of ethyl acetate and hexane to give a white solid. The solid was collected, rinsed with hexane and recrystallized from a mixture of chloroform and hexane to give 0.7 g of white solid 5-{2-[(3,5-di-t-butylphenoxy)-methyl]phenyl}tetrazole, m.p. 151°–153° C. Analysis: Calculated for $C_{22}H_{28}N_4O$: %C, 72.5; %H, 7.7; %N, 15.4; Found: %C, 72.8; %H, 8.0; %N, 15.5.

EXAMPLE 7

Preparation of 2-(3,5-Di-t-butylphenoxymethyl)benzoic Acid

A mixture of 6.4 g (0.02 mole) of 2-(3,5-di-t-butylphenoxymethyl)-1-benzenecarbonitrile, 1 g (0.05 mole) of 90% potassium hydroxide and 40 ml of 2-methoxyethanol was heated at 130° C. for about sixteen hours. Since a majority of the nitrile appeared to be undissolved, the temperature was raised to 145° C. and the heating was continued for an additional 72 hours. The reaction mixture was allowed to cool to room temperature before being poured into 300 ml 10% hydrochloric acid. The resulting oily brown solid was decolorized with activated charcoal and recrystallized twice from ethanol to give 0.8 g of white solid 2-(3,5-di-t-butylphenoxymethyl)benzoic acid, m.p. 173°–174° C. Analysis: Calculated for $C_{22}H_{28}O_3$: %C, 77.6; %H, 8.3; Found: %C 77.5; %H, 8.5.

EXAMPLE 8

Preparation of 2-(3,5-Di-t-butylphenoxymethyl)-N-(tetrazol-5-yl)benzamide

A solution of 3.40 g (0.01 mole) of 2-(3,5-di-t-butylphenoxymethyl)benzoic acid and 1.03 g (0.01 mole) of 5-aminotetrazole in 30 ml of pyridine was treated with a dropwise addition of 2.36 g (0.02 mole) of thionyl chloride. The resulting solution was stirred for forty minutes before being diluted with 300 ml of 5% hydrochloric acid to give a gum which slowly crystallized. The solid was collected, rinsed with water and recrystallized from aqueous dimethylformamide to give 1.3 g of white solid 2-(3,5-di-t-butylphenoxymethyl)-N-(tetrazol-5-yl)benzamide, m.p. 251°–254° C.. Analysis: Calculated for $C_{23}H_{29}N_5O_2$: %C, 67.8; %H, 7.2; %N, 17.2; Found: %C, 67.7; %H, 7.1; %N, 17.2.

EXAMPLE 9

Preparation of 3-(3,5-Di-t-butylphenoxymethyl)-1benzenecarbonitrile

Using the method of Example 1, 20.6 g (0.10 mole) of alpha-bromo-m-tolunitrile was reacted with 3,5-di-t-butylphenol to give white crystalline 3-(3,5-di-t-butylphenoxymethyl)-1-benzenecarbonitrile. Analysis: Calculated for $C_{22}H_{27}NO$: %C 82.2; %H, 8.4; %N, 4.4; Found: %C, 82.2; H, 8.5; %N, 4.1.

EXAMPLE 10

Preparation of 5-{3,5-Di-t-butylphenoxy)methyl]phenyl}-tetrazole

Using the method of Example 2, 3.2 g (0.01 mole) of 3-(3,5-di-t-butylphenoxymethyl)-1-benzenecarbonitrile was reacted to give 0.5 g of white solid 5-{3-[(3,5-di-t-butylphenoxy)methyl]phenyl}tetrazole hemihydrate, m.p. 165°–167° C. Analysis: Calculated for $C_{22}H_{28}N_4O$ ½$H_2O$; %C, 70.7; %H, 7.8; %N, 15.0; Found: %C, 70.9; %H, 7.9; %N, 15.0.

EXAMPLE 11

Preparation of 3-(3,5-Di-t-butylphenoxymethyl)benzoic Acid

Using the method of Example 3, 6.4 g of 3-(3,5-di-t-butylphenoxymethyl)-1-benzenecarbonitrile was hydrolyzed to give 2.5 g of light brown solid 3-(3,5-di-t-butylphenoxymethyl)benzoic acid, m.p. 167°–169° C. Analysis: Calculated for $C_{22}H_{28}O_3$: %C, 77.6; %H, 8.3; Found: %C, 77.6; %H, 8.6.

EXAMPLE 12

Preparation of 5-(3,5-Di-t-butylphenoxy)pentanenitrile

Using the method of Example 1, 17.8 g (0.11 mole) of 5-bromo-pentanenitrile was reacted with 20.6 g (0.10 mole) of 3,5-di-t-butylphenol to give 17.8 g of white crystalline 5-(3,5-di-t-butylphenoxy)pentanenitrile, m.p. 61°–64° C. Analysis: Calculated for: $C_{19}H_{29}NO$: %C, 79.4; , %H, 10.2; %N, 4.9; Found: %C, 79.0; %H, 10.3; %N, 5.1.

EXAMPLE 13

Preparation of 5-(3,5-Di-t-butylphenoxy) pentanoic Acid

Using the method of Example 3, 5.74 g of 5-(3,5-di-t-butylphenoxy)pentanenitrile was hydrolyzed to give 1.1 g of white crystalline 5-(3,5-di-t-butylphenoxy)pentanoic acid, m.p. 113°–115° C. Analysis: Calculated for $C_{19}H_{30}O_3$: %C, 74.5; %H, 9.9; Found, %C, 74.9; %H, 9.9.

EXAMPLE 14

Preparation of 5-[4-(3,5-Di-t-butylphenoxy)butyl]tetrazole

A mixture containing 2.87 g (0.10 mole) of 5-(3,5-di-t-butylphenoxy)pentanenitrile, 1.95 g (0.03 mole) sodium azide, 1.60 g (0.03 mole) ammonium chloride, 0.42 g (0.01 mole) lithium chloride and 25 ml of dimethylformamide was heated at 120° C. in a stoppered flask for about sixteen hours. Analysis of the reaction mixture by high pressure liquid chromatography revealed that the reaction still contained nitrile. The reaction was recharged with 1.95 g of sodium azide and 1.60 g of ammonium chloride and heated for an additional sixteen hours. The reaction mixture was poured into 250 ml of water. The resulting precipitate was collected, rinsed with water, air dried and recrystallized twice from aqueous methanol to give 1.8 g of white solid 5-[4-(3,5-di-t-butylphenoxy)butyl]tetrazole, m.p. 140°–141° C.

Analysis: Calculated for $C_{19}H_{30}N_4O$: %C, 69.1; %H, 9.2; %N, 17.0; Found: %C, 69.0; %H, 9.1; %N, 17.1.

EXAMPLE 15

Preparation of 7-(3,5-Di-t-butylphenoxy)heptanenitrile

A mixture containing 20.6 g (0.10 mole) of 3,5-di-t-butylphenol, 20.9 g (0.11 mole) of 7-bromoheptanenitrile, 4.0 g (0.10 mole) of sodium hydroxide and 250 ml of dimethylformamide was heated at 120° C. for about forty hours. The solvent was evaporated and the residue was added to 250 ml of water. The resulting oil was separated and dissolved in 250 ml of diethyl ether. The ether solution was washed twice with 250 ml portions of 10% sodium hydroxide, washed once with 250 ml water, dried over magnesium sulfate, and evaporated to give an oil which solidified on standing. The solid was recrystallized twice from methanol. The structure was confirmed by nuclear magnetic resonance spectroscopy.

EXAMPLE 16

Preparation of 5-[6-(3,5-Di-t-butylphenoxy)hex-1-yl]tetrazole

Using the method of Example 2, 2.15 g (0.01 mole) of 7-(3,5-di-t-butylphenoxy)heptanenitrile was reacted to give 2.5 g of white solid 5-[6-(3,5-di-t-butylphenoxy)-hex-1-yl]tetrazole, m.p. 113°–115° C. Analysis: Calculated for $C_{21}H_{34}N_4O$: %C, 70.4; %H, 9.6; %N, 15.6; Found: %C, 70.7; %H, 9.6; %N, 15.8.

EXAMPLE 17

Preparation of 7-(3,5-Di-t-butylphenoxy)heptanoic Acid

Using the method of Example 3, 6.30 g (0.02 mole) of 7-(3,5-di-t-butylphenoxy)heptanenitrile was hydrolyzed to give 1.9 g of white crystalline 7-(3,5-di-t-butylphenoxy)heptanoic acid, m.p. 88°–90° C. Analysis: Calculated for $C_{21}H_{34}O_3$: %C, 75.4; %H, 10.3; Found: %C, 75.4; %H, 10.4.

What is claimed is:

1. A compound of the formula

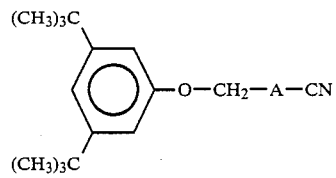

wherein A is phenylene or an alkylene group containing two to about seven carbon atoms.

* * * * *